United States Patent [19]

Sandhaus

[11] 4,394,864
[45] Jul. 26, 1983

[54] APPARATUS AND METHOD FOR EFFECTING OCCLUSION OF THE VAS DEFERENS

[76] Inventor: Jeffrey Sandhaus, Rte. 9W, Snedens Landing, Palisades, N.Y. 10964

[21] Appl. No.: 254,393

[22] Filed: Apr. 15, 1981

[51] Int. Cl.³ .................. A61B 17/12; A61B 17/28
[52] U.S. Cl. .................................. 128/321; 128/325; 227/DIG. 1
[58] Field of Search .......... 128/346, 325, 321, 303 R; 227/DIG. 1

[56] References Cited

U.S. PATENT DOCUMENTS

| 2,307,377 | 1/1943 | Riccardi | 128/346 |
| 3,270,745 | 9/1966 | Wood | 128/325 |
| 3,631,859 | 1/1972 | Crutchfield | 128/346 |
| 3,895,636 | 7/1975 | Schmidt | 128/347 X |
| 4,026,294 | 5/1977 | Mattler | 128/346 X |
| 4,169,476 | 10/1979 | Hiltebrandt | 128/346 X |
| 4,242,902 | 1/1981 | Green | 128/325 X |
| 4,246,903 | 1/1981 | Larkin | 128/325 |

FOREIGN PATENT DOCUMENTS

| 627970 | 3/1936 | Fed. Rep. of Germany | 128/325 |
| 735249 | 6/1980 | U.S.S.R. | 128/346 |

*Primary Examiner*—Michael H. Thaler
*Attorney, Agent, or Firm*—Steinberg & Raskin

[57] ABSTRACT

Apparatus for accomplishing the permanent placement of a silicone locking clip having dentate edges around the vas deferens to interrupt the continuity of the same in a rapid, safe and minimally invasive manner. The apparatus includes a trocar-type instrument in which the locking clip is enclosed for delivery to a position proximate to the vas whereupon the jaw members of the trocar-type instrument are opened whereby the clip is opened to an extent such that the vas is receivable therein whereupon the jaw members are closed to lock the clip onto the vas to occlude the same.

18 Claims, 11 Drawing Figures

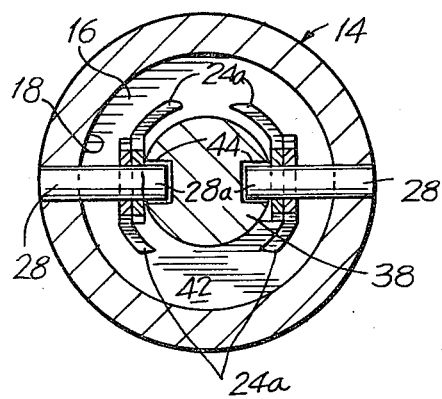
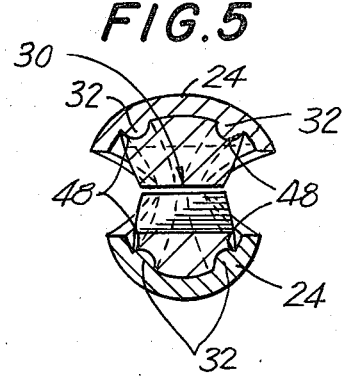
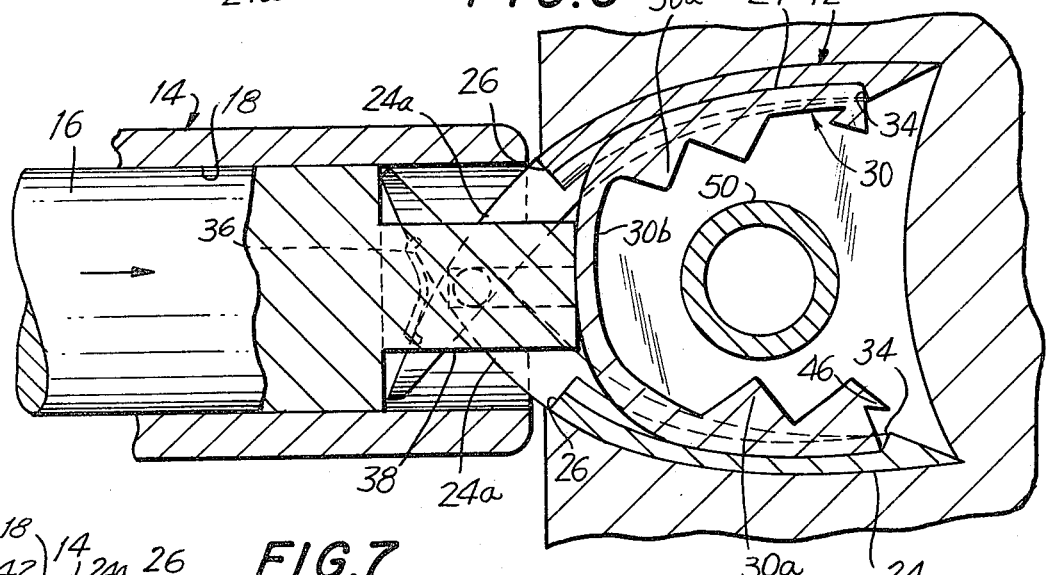
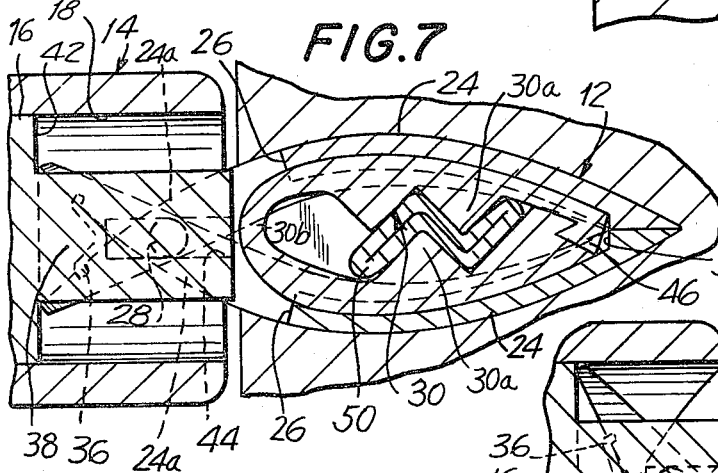
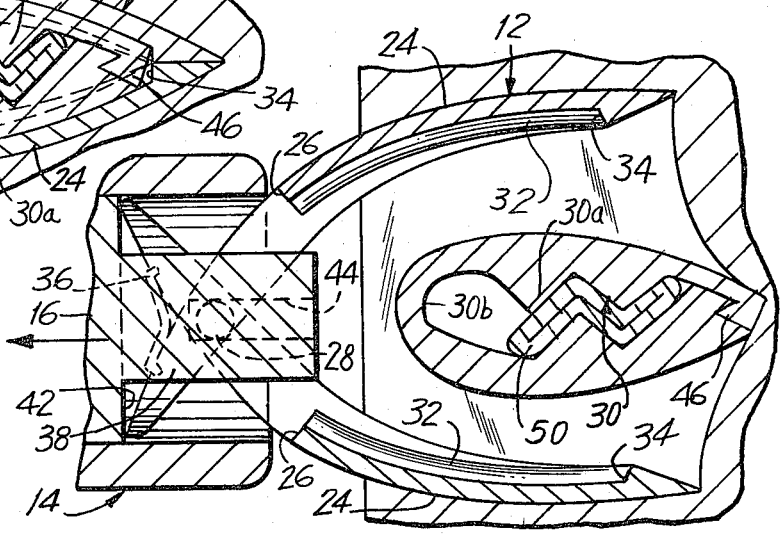

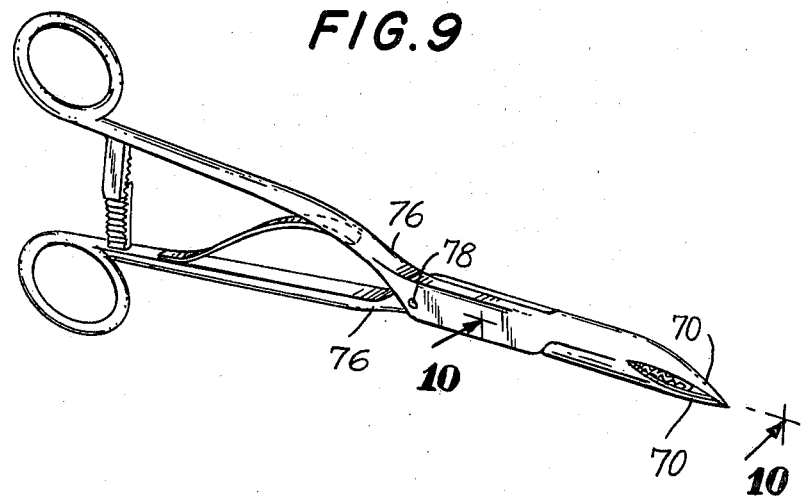
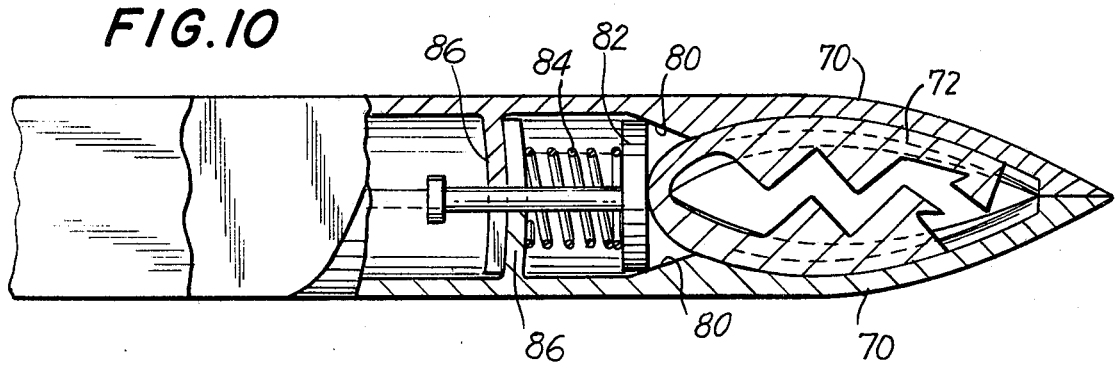
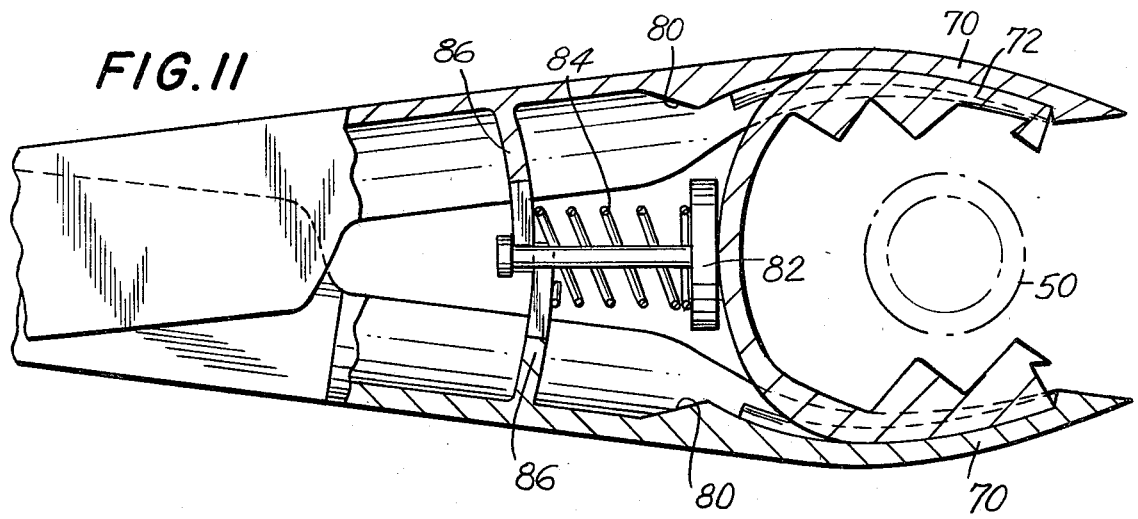

APPARATUS AND METHOD FOR EFFECTING OCCLUSION OF THE VAS DEFERENS

BACKGROUND OF THE INVENTION

This invention relates generally to apparatus for occluding vessels in the body and, more particularly, to apparatus for occluding the vas deferens in a vasectomy in a rapid, safe and minimally invasive manner.

The procedure generally followed in simple vasectomies comprises identifying and then grasping the vas deferens with an appropriate instrument whereupon an incision is made through the subcutaneous tissue adjacent thereto. The vasal sheath is grasped with a clamp and incised with the vas being dissected from the sheath. The vas is then clamped and a segment excised whereupon the distal end of the vas is electrocoagulated, ligated, and then buried within the vasal sheath. The proximal end of the vas is electrocoagulated and ligated. Finally, the skin is closed.

Although this procedure has proven to be quite reliable, it is subject to certain disadvantages. More particularly, the above-described procedure is relatively time consuming, requiring on the order of about forty minutes. The conventional procedure requires a surgical incision which requires all of the precautions normally incident to relatively complicated surgical procedures to be adhered to.

SUMMARY OF THE INVENTION

Accordingly, one object of the present invention is to provide new and improved apparatus for use in occluding a vessel in the body, and particularly for occluding the vas deferens in a vasectomy.

Another object of the present invention is to provide new and improved apparatus for occluding the vas deferens in a vasectomy in a rapid, safe and minimally invasive manner.

In accordance with the present invention, these and other objects are attained by providing apparatus whereby a silicone locking clip can be permanently placed around and locked on the vas deferens to interrupt the continuity of the same.

In one embodiment, the apparatus includes a tocar-type locking clip delivering instrument constituted by a pair of jaw members which are pivotally affixed to each other so as to be actuatable between closed and opened positions. The jaw members each taper in a forward direction to a sharp point such that the clip delivering instrument in its closed position constitutes a sharp pointed instrument for penetrating the body tissue. A substantially U-shaped silicone locking clip is enclosed within an interior space defined between the jaw members. The locking clip is releasably affixed in the space between the jaw members in a manner such that when the instrument is in a closed position and the clip is in a first retracted position therewithin, the clip will be in an unlocked mode. When the instrument is actuated to an open position, the clip itself is opened to an extent such that the vas is receivable therein. The instrument is then actuated to a closed position and the clip moved to a second advanced position therewithin whereupon the clip is closed and locked onto the vas.

In one embodiment, the pair of jaw members defining the trocar-type tip are pivotally interconnected by a pair of pivot pins which are fixed to the inner surface of an elongate sheath. An elongate obturator is slidably received within the bore of the sheath and has a forward end region defining a substantially annular camming surface which is adapted to contact cam portions of the jaw members in a manner such that upon advancement of the obturator within the bore of the sheath, the jaw members are moved to the open position. Further, a forward projecting portion is provided on the front end of the obturator which is adapted to contact the clip enclosed within the trocar-type tip and urge the clip from the retracted to the advanced position, preferably simultaneously with the pivoting of the jaw members to the open position.

The vas is then positioned within the open clip which is then closed under the biasing of a spring or the like. The vas clip is self locking so that when it is situated in its advanced position within the trocar-type tip, the closure of the latter will result in the clip locking over the vas to occlude the same.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which:

FIG. 4 is a section view taken along line 4—4 of FIG. 2;

FIG. 5 is a section view taken along line 5—5 of FIG. 2;

FIG. 6 is a view similar to FIG. 2 and illustrating the vas being received within the locking clip prior to the latter being locked thereon;

FIG. 7 is a view similar to FIG. 6 and illustrating the locking clip being locked over the vas;

FIG. 8 is a view similar to FIG. 7 and illustrating the withdrawal of the apparatus subsequent to the locking clip being locked over the vas;

FIG. 9 is a perspective view of another embodiment of the present invention;

FIG. 10 is a section view taken along line 10—10 of FIG. 9; and

FIG. 11 is a view similar to FIG. 10 and illustrating the apparatus as the vas is received in the locking clip.

DESCRIPTION OF THE PREFERRED EMBODIMENTS

Figure 1:
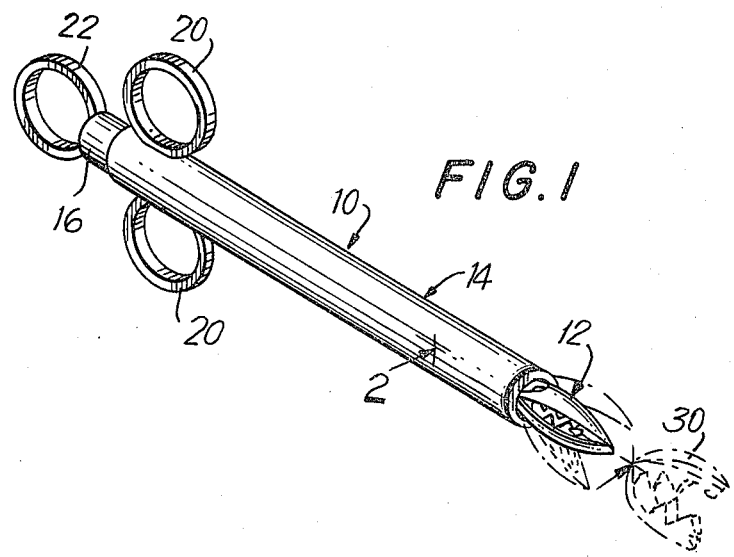
FIG. 1 is a perspective view of one embodiment of the present invention, the open position of the trocar-type tip as well as the locking clip being illustrated in phantom.

Referring now to the drawings wherein like reference characters designate identical or corresponding parts throughout the several views, the apparatus for effecting vas occlusion, generally designated 10, is illustrated in FIG. 1.

In the illustrated embodiment, apparatus 10 includes an instrument 12 for delivering a locking clip into occluding relationship with the vas, an outer elongate sheath 14 to the forward end of which the clip delivering instrument 12 is connected, and an elongate obturator 16 (FIG. 2) slidably received within the bore 18 of sheath 14. A pair of rings 20 are fixed to opposed sides of sheath 14 while a ring 22 is fixed to the rearward end of obturator 16, the rings being adapted to receive the fingers of the physician in order to slide the obturator forwardly during the occluding procedure as described in greater detail below.

Referring to FIGS. 2-5, the locking clip delivering instrument 12 is constituted by a pair of jaw members 24 pivotally connected to each other for pivotal actuation between a closed position (FIG. 2) and an open position (FIG. 6). Each of the jaw members 24 has a concave transverse cross section as seen in FIG. 5, and a bowed longitudinal cross section, tapering to a point at its forward end. In this manner the clip delivering instrument 12 constitutes a sharp pointed instrument capable of penetrating body tissue and in this respect functions as a trocar-type instrument.

The inwardly concave surface structure of each jaw member 24 terminates at a rearwardly facing edge 26 from which a pair of lateral fingers 24a extend generally following the longitudinal curvature of the jaw member. Each lateral finger 24a has a portion which passes laterally adjacent to a corresponding portion of a respective one of the lateral fingers 24a of the other jaw member 24 as best seen in FIG. 4. The jaw members 24 are pivotally interconnected by a pair of pivot pins 28, each of which passes through aligned openings formed in the laterally adjacent portions of a respective pair of lateral fingers 24a.

As seen in FIG. 4, the pivot pins 28 are fixed in sheath 14 and extend radially inwardly passing through aligned openings formed in the respective pairs of laterally adjacent portions of fingers 24a. The innermost portion 28a of each pivot pin 28 extends inwardly beyond the lateral fingers 24a.

The pair of jaw members 24 define an interior space between them for accommodating a substantially U-shaped locking clip 30. The inner surface of each jaw member 24 is formed with a pair of longitudinally extending ribs 32 as best seen in FIG. 5 whose purpose will be made clear hereinbelow. The ribs 32 extend from the rearward edge 26 and forwardly terminate at a stop surface 34.

Figure 2:
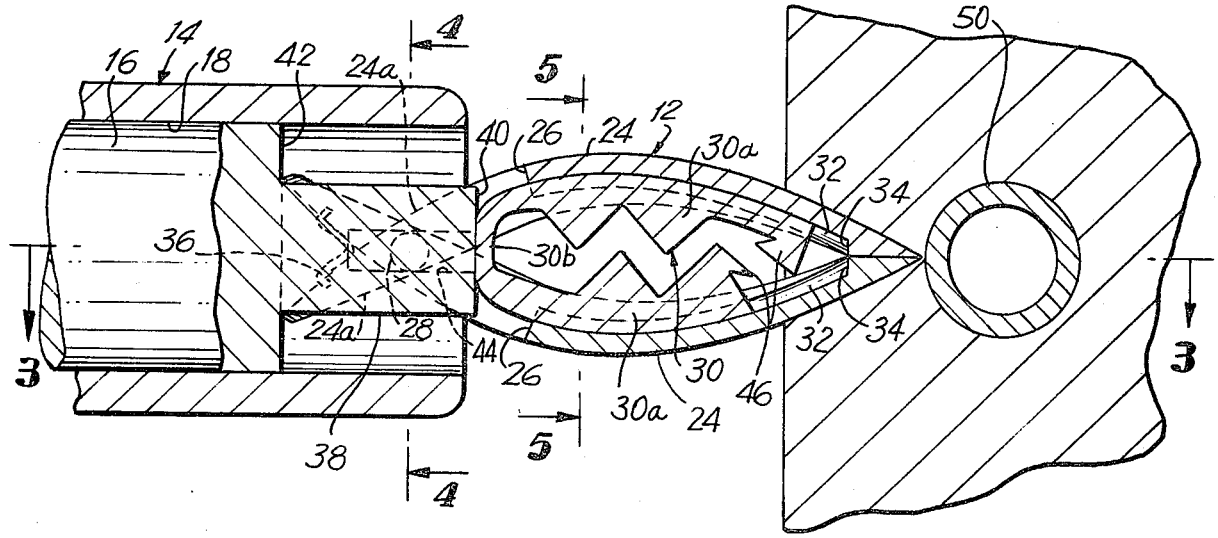
FIG. 2 is a section view taken along line 2—2 of FIG. 1 and showing the apparatus in use prior to the vas being occluded.
Figure 3:
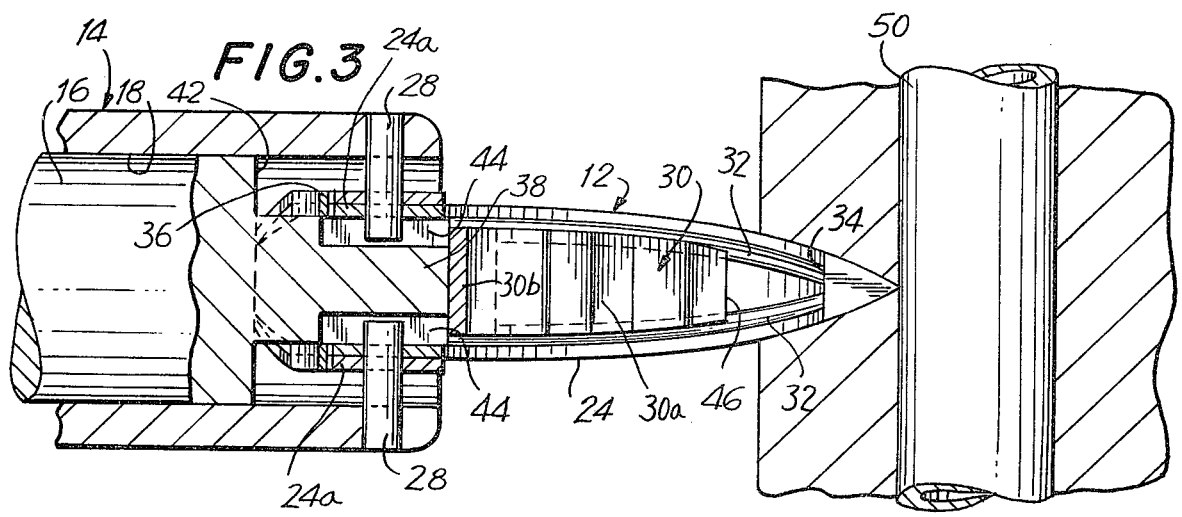
FIG. 3 is a section view taken along line 3—3 of FIG. 2.

As noted above, the clip delivering instrument 12 is connected to the forward end of sheath 14 by pivot pins 28. The sheath bore 18 communicates with the interior spaced defined between the jaw members 24 through the opening defined between the lateral fingers 24a and rearward edges 26 of jaw members 24. A leaf spring 36 is provided between the rearwardly extending lateral fingers 24a as seen in FIG. 2 to normally bias the jaw members 24 towards the closed position.

The elongate obturator 16 is slidably received within the bore 18 of sheath 14 extending from the rear thereof as seen in FIG. 1. The obturator 16 has a forward end region having a reduced diameter projecting portion 38 having a forwardly facing surface 40 and also defining with the body of obturator 16 a forwardly facing annular surface 42. As seen in FIG. 2, with the jaw members 24 closed, the obturator 16 can be advanced until the annular surface 42 contacts the rear edge surfaces of the lateral fingers 24a with the projecting portion 38 being situated between them. Further forward movement of obturator 16 results in the annular surface 42 pushing against the rear surfaces of lateral fingers 24a in a manner such that the jaw members 24 are pivoted to their open position against the force of spring 36 as best seen in FIG. 6. In this manner, the annular surface 42 and rear edge surfaces of lateral fingers 24a act as camming surfaces. It will be understood that retraction or rearward movement of obturator 16 will result in the jaw members 24 moving to their closed position under the force of spring 36.

A pair of opposed longitudinally extending slots 44 are formed in projecting portion 38 extending rearwardly from the forward surface 40 thereof which receive the inner portions 28a of pivot pins 28 in order to provide a clearance for the advancement of obturator 16 during the opening of the clip delivering instrument 12 as described above.

The locking clip 30 is preferably formed of silicone or other biologically acceptable material and comprises a pair of leg portions 30a and an intermediate portion 30b connecting the leg portions 30a. The leg portions have an inwardly facing dentate configuration. A pair of barbs 46 are formed at the free ends of leg portions 30a which are adapted to lock with each other when the free ends of the clip are opposed as seen in FIGS. 7 and 8. The material from which the clip is formed, e.g., silicone, is resilient and the clip in its unstressed form has an open configuration as seen in FIG. 1. Further, the outer surface of each of the leg portions 30a of clip 30 is formed with a pair of longitudinally extending channels 48 as seen in FIG. 5. The channels 48 are suitably positioned so as to receive the ribs 32 of jaw members 24 when the clip is situated within the interior space between jaw members 24 as described below. The structure of the ribs 32 and channels 48 is such that when the clip is located between jaw members 24 as shown in FIGS. 2 and 5, the leg portions 30a are removably affixed to the respective jaw members 24. More particularly, so long as the clip is unlocked, i.e., the barbs 46 do not engage each other, the leg portions 30a of the clip will follow both the opening and closing movement of the jaw members 24. For example, the ribs 32 might be designed so as to "snap" into the respective channels 48. However, once the clip is locked and a sufficient opening force applied to jaw members 24, the ribs 32 will separate from within the channels 48.

The surgical procedure wherein the apparatus of the present invention is utilized for effecting vas occlusion, i.e., a vasectomy, will now be described. With the obturator in a retracted position, i.e., positioned somewhat rearwardly of the position shown in FIG. 2, the locking clip 30 is situated within the clip delivering instrument 12 in the position shown in FIG. 2 with the leg portions 30a thereof removably affixed to the jaw members 24 as described above. The jaw members 24 are allowed to close under the force of spring 36. The obturator 16 is then advanced to the position illustrated in FIG. 2. wherein the annular camming surface 42 just engages the rear edge camming surface of the lateral fingers 24a of jaw members 24. It is to be noted that when the obturator 16 attains this position, the forward surface 40 of the projecting portion 38 just engages the rear of the intermediate portion 30b. The innermost portions 28a of pivot pin 28 are received within slots 44 as noted above. In this connection, the sheath and obturator may be provided with interlocking longitudinally extending key structure of prevent rotation of the obturator with respect to the sheath.

It is to be noted that when the locking clip 30 is situated within the delivering instrument 12 as described above, the forward barb ends of the clip are spaced from each other and from the stop surfaces 34 of jaw members 24 so that clip is in an open mode or configuration.

An alternative method of "loading" the clip into the clip delivering instrument 12 is possible by inserting the clip into the rear end of the sheath bore 18 and then pushing the clip using obturator 16 through the bore 18 and into the interior space of instrument 12 through the space defined between the lateral fingers 24a. In this connection, the angular position of the clip with respect to the sheath can be fixed by means of longitudinally extending score lines or the key structure described above.

After sterilizing the region of the intended vasectomy, the vas 50 is located and firmly held by the physician wherupon the tip of the trocar-type clip delivering instrument 12 is introduced through the tissue until the vas is approximated, taking care not to pierce the same.

The obturator 16 is then depressed and moved forwardly within the sheath 14. Such action results in two separate actions occurring simultaneously. Thus, the annular camming surface 42 is urged against the camming surface of lateral fingers 24a to open the jaw members 24. Simultaneously, the forward surface 40 of projecting portion 38 pushes against the intermediate portion 30b of locking clip 30 to advance the latter within instrument 12. By virtue of the removable affixation of the leg portion 30a of clip 30 to the respective jaw members 24, the clip 30 will be further opened to an extent whereby the vas 50 can be received between the leg portions of the clip. The obturator 16 is advanced until the free ends of the clip abut against the stop surfaces 34 of jaw members 24 so that the clip 30 is moved from its retracted position shown in FIG. 2 to an advanced position. After the instrument 12 and clip held therewithin are opened as described above, the apparatus and vas are manipulated until the latter is situated between the leg portions of the opened clip. FIG. 6 illustrates the configuration of the apparatus with respect to the vas at this stage of the procedure.

The jaw members 24 are then closed by retracting the obturator 16 (or advancing the sheath 14) so that the jaw members 24 pivotally close under the force of spring 36. As seen in FIG. 7, by virtue of its advanced position within instrument 12, closure of the jaw members will result in the barbs 46 of the clip locking to each other thereby locking the clip 30 around the vas deferens 50.

The jaw members 24 are then again opened by advancing obturator 16 (or retracting sheath 14). However, since the clip 30 is now locked around the vas, the leg portions of the clip will separate from the jaw members 24, i.e., the ribs 32 will withdraw from the channels 48, leaving the clip 30 locked on the vas as seen in FIG. 8. The apparatus is then withdrawn from the puncture incision. The vas clip locked over the vas deferens occludes the latter preventing the passage of sperm from the testis to the ejaculatory duct.

The present invention accomplishes the occlusion of the vas in a rapid manner, typically under one minute, with minimum invasion of the body. The entire apparatus is relatively small being approximately the size of a ball-point pen and may be entirely disposable after the vasectomy is accomplished.

Another embodiment of the present invention is illustrated in FIGS. 9-11. In this embodiment, the apparatus includes a clip delivering instrument comprising a pair of jaw members 70 having the same general configuration as jaw members 24 of the embodiment discussed above. Thus, each of the jaw members tapers in a forward direction to a sharp point such that when the clip delivering instrument is in its closed position, a sharp pointed instrument is defined for penetrating body tissue. The pair of jaw members 70 defines an interior space between them for accommodating a substantially U-shaped locking clip 72. Ribs 74 are provided on the inner surfaces of jaw members 70 and are received with matching channels provided in the locking clip 72.

Each of the jaw members 70 is integrally formed at one end of a respective handle member 76, handle members 76 being pivoted to each other at 78. Thus, the jaw members 70 can be moved between open and closed positions by a physician inserting the appropriate fingers through the handle loops and pivoting the handle members in a conventional fashion.

Each of the jaw members 70 terminates at its rearward end with an inwardly and forwardly tapering surface 80. A push member 82 is biased by means of a spring 84 against the surface 80 as seen in FIG. 10, the push member 82 being mounted for axial movement by means of cooperating members 86 integral with handle members 76.

As seen in FIG. 10, the clip 72 is positioned between the jaw members 70 in engagement with push member 82. After making the puncture incision, the jaw members 70 are opened whereupon the surfaces 80 move out of their obstructing position thereby allowing the push member 82 to move forwardly under the force of spring 84. In this manner the clip 72 is advanced from a retracted to an advanced position within the instrument. The jaw members 70 can then be closed whereupon the clip will be locked over the vas deferens 50. Reopening of the jaw members leaves the clip locked over the vas in the same manner as discussed above in connection with the previous embodiment of the invention.

Although the foregoing description is specifically directed to the use of the present invention in connection with occluding the vas deferens in a vasectomy, it is understood that the apparatus of the invention may be used in connection with other applications.

Obviously, numerous modifications and variations of the present invention are possible in the light of the above teachings. It is therefore to be understood that within the scope of the claims appended hereto, the invention may be practiced otherwise than is specifically disclosed herein.

What is claimed is:

1. Apparatus for effecting occlusion of a vessel in the body, particularly the vas deferens in a vasectomy, comprising:

a locking clip delivering instrument including a pair of jaw members pivotally coupled to each other for pivotal actuation between closed and open positions, said jaw members each tapering in a forward direction to a sharp point such that said clip delivering instrument, when said jaw members are in the closed position, constitutes a sharp pointed instrument capable of puncturing body tissue, said pair of jaw members defining an interior space between them for receiving a substantially U-shaped locking clip, said interior space tapering in the direction towards said pointed ends of said jaw members when said jaw members are in the closed position and having a longitudinal dimension, such that the clip is movable within said interior space between a first retracted position distal form said pointed ends of said jaw members and a second advanced position proximal to said pointed ends of said jaw members;

means for movably mounting the U-shaped locking clip in said first retracted position within said interior space between said jaw members when said jaw members are in the closed position;

means for actuating said jaw members from the closed position to the open position;

means for advancing the U-shaped locking clip from said first retracted position to said second advanced position proximal to said pointed ends of said jaw members; and means for actuating said jaw members from the open position to the closed position with said U-shaped clip in said second advanced position.

2. The combination of claim 1 wherein said clip delivering instrument further includes an elongate sheath having a bore formed therethrough and a pair of aligned pivot pins, each pivot pin being fixed to said sheath and laterally extending into said bore at a forward end thereof and pivotally affixing said pair of jaw members to each other at respective lateral sides thereof.

3. The combination of claim 2 wherein said jaw members include cam portions extending rearwardly of said pivot pins.

4. The combination of claim 3 wherein said actuating means comprises an elongate obturator slidably received within the bore of said sheath, said obturator having a forward end region defining a substantially annular camming surface adapted to contact said jaw member cam portions upon advancement of said obturator within the bore of said sheath to pivot said jaw members to the open position.

5. The combination of claim 4 wherein said actuating means further includes spring means for normally biasing said jaw members toward the closed position.

6. The combination of claim 4 wherein the jaw members together define a rearward facing opening into the interior space and wherein said means for advancing the clip from said first retracted position to said second advanced position includes a projecting portion formed at the forward end region of said obturator adapted to be received into said rearward facing opening as said obturator is advanced within the bore of said sheath whereby the clip is contacted by said projecting portion and advanced from said first retracted to said second advanced position.

7. The combination of claim 6 wherein said camming surface and projecting portion of said obturator are formed such that upon advancement of said obturator within the bore of said sheath said jaw members are pivoted to the open position and the clip is advanced to said second advanced position substantially simultaneously.

8. The combination of claim 7 wherein portions of said pivot pins extend inwardly beyond inner surfaces of said jaw members and wherein a pair of opposed slots are formed in said projecting portion which are receivable of said inwardly extending portions of said pivot pins.

9. The combination of claim 6 wherein each of said jaw members includes a forward stop surface for defining said second advanced position of the clip.

10. Apparatus as recited in claim 1 further comprising:
a U-shaped locking clip including a pair of opposed leg portions and an intermediate portion connecting first respective ends of said leg portions, said locking clip including means for automatically locking said leg portions to each other when second respective ends of said leg portions are brought into proximate relationship with each other, and wherein said interior space and locking clip are shaped such that when said clip is within said interior space in said first retracted position and said jaw members are in the closed position, said clip leg portions remain unlocked to each other and when said clip is within said interior space in said second advanced position and said jaw members are actuated to the closed position, said second respective ends of said leg portions are brought into proximate relationship with each other to thereby lock said clip leg portions to each other.

11. The combination of claim 10 further including means for releasably affixing each of said pair of opposed leg portions of the U-shaped locking clip to the inwardly facing surface of a respective one of said jaw members so that upon actuation of said jaw members to the open position said opposed clip leg portions are further opened, said affixing means permitting movement of said clip from said first retracted position to said second advanced position with said clip leg portions remaining affixed to said respective jaw members.

12. The combination of claim 11 wherein each of said jaw members has an arcuate transverse cross-section.

13. The combination of claim 1 wherein said clip delivering instrument further includes a pair of handle members, each having a respective jaw member integrally formed at one end thereof, said handle members being pivotally connected to each other and further constituting said actuating means.

14. The combination of claim 13 wherein said jaw members together define a rearward facing opening into the interior space and wherein said means for advancing the clip from said first retracted position to said second advanced position comprises a pusher member mounted in said clip delivering instrument rearwardly of the interior space defined between said jaw members, spring means for normally biasing said pusher member towards said interior space and stop surfaces adapted to engage said pusher member and prevent movement thereof into the interior space while said jaw members are closed and adapted to disengage from said pusher member and allow movement thereof into the interior space when said jaw members are opened thereby contacting said clip and advance the same to said advanced position.

15. Apparatus for occluding a vessel in a body, particularly the vas deferens in a vasectomy, comprising:
a locking clip delivering instrument including a pair of jaw members pivotally coupled to each other for pivotal actuation between closed and open positions, said jaw members each tapering in a forward direction to a sharp point such that said clip delivering instrument, when said jaw members are in the closed position, constitutes a sharp pointed instrument capable of puncturing body tissue, said pair of jaw members defining an interior space between them for receiving a substantially U-shaped locking clip, said interior space tapering in the direction towards said pointed ends of said jaw members when said jaw members are in the closed position, a substantially U-shaped locking clip of the self-locking type positionable within said interior space between said jaw members such that when said jaws are in a closed position and said clip is in a position distal from said pointed ends of said jaw members, said clip is in an unlocked mode and when said instrument is actuated to an open position the clip is opened to an extent such that the vessel to be occluded is receivable therein;

means for actuating said jaw members between closed and opened positions; and means for positioning the clip member within said interior space between said jaw members to a position proximal to said pointed ends of said jaw members such that when said jaw members are actuated to the closed position, said clip is closed and locked.

16. The combination of claim 15 wherein said clip includes a pair of leg portions and an intermediate portion connecting said leg portions, said leg portions having respective free ends adapted to lock to each other to lock the clip when said free ends are brought into approximation.

17. The combination of claim 15 wherein said locking clip is formed of silicone.

18. A method for effecting occlusion of a vessel in a body utilized a U-shaped self-locking clip and a clip delivering instrument including a pair of jaw members pivotally coupled to each other for pivotal actuation between closed and open positions, the jaw members each tapering in a forward direction to a sharp point such that the clip delivering instrument, when the jaw members are in the closed position, constitutes a sharp pointed instrument capable of penetrating body tissue, the pair of jaw members defining an interior space between them for receiving the U-shaped locking clip, the interior space tapering in the direction towards the pointed ends of the jaw members when the jaw members are in the closed position, comprising the steps of:

situating the clip within the interior space between said jaw members at a first retracted position therewithin distal from the pointed ends of the jaw members wherein with the jaw members in the closed position, the clip is unlocked;

puncturing the skin with the sharp point of the instrument defined by the sharp points of the jaw members in the closed position and positioning the point proximate to the vessel to be occluded;

pivotally actuating the jaw members to the open position and moving the clip member to a second advanced position proximal to the pointed ends of the jaw members within the interior space defined between them;

positioning the clip around the vessel to be occluded;

pivotally actuating the jaw members to the closed position with the self-locking clip in the second advanced position to thereby lock the clip on the vessel;

pivotally actuating the jaw members to the open position while the clip remains locked on the vessel; and withdrawing the instrument from the skin puncture.

* * * * *